US010973602B2

(12) United States Patent
Hillas et al.

(10) Patent No.: US 10,973,602 B2
(45) Date of Patent: Apr. 13, 2021

(54) POUCHES WITH MULTI-LAYER WALLS FOR IMPROVED DURABILITY AND PROTECTION OF MEDICAL DEVICES

(71) Applicant: Medtronic Vascular, Inc., Santa Rosa, CA (US)

(72) Inventors: Joshua Hillas, Ballybrit (IE); David Clarke, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 16/442,582

(22) Filed: Jun. 17, 2019

(65) Prior Publication Data

US 2019/0298473 A1    Oct. 3, 2019

Related U.S. Application Data

(62) Division of application No. 15/716,859, filed on Sep. 27, 2017, now Pat. No. 10,321,967.

(60) Provisional application No. 62/400,205, filed on Sep. 27, 2016.

(51) Int. Cl.
*B65D 81/05* (2006.01)
*A61B 50/30* (2016.01)
*A61L 2/20* (2006.01)

(52) U.S. Cl.
CPC .............. *A61B 50/30* (2016.02); *A61L 2/206* (2013.01); *B65D 81/052* (2013.01); *A61B 2050/316* (2016.02)

(58) Field of Classification Search
CPC ...... B65D 81/03; B65D 81/052; A61B 50/30; A61B 2050/316

USPC ......................................................... 206/522
See application file for complete search history.

(56) References Cited

U.S. PATENT DOCUMENTS

| 3,552,638 A | 1/1971 | Quackenbush |
| 3,991,881 A | 11/1976 | Augurt |
| 4,270,658 A | 6/1981 | Schuster |
| 4,407,874 A | 10/1983 | Gehrke |
| 4,465,188 A * | 8/1984 | Soroka ............... B65D 81/052 |
| | | 206/521 |

(Continued)

FOREIGN PATENT DOCUMENTS

| DE | 19 41 545 A1 | 7/1970 |
| DE | 42 29 314 A1 | 3/1994 |

(Continued)

OTHER PUBLICATIONS

International Search Report dated Jan. 4, 2018 in corresponding International Patent Application No. PCT/US2017/053656.

(Continued)

*Primary Examiner* — Steven A. Reynolds

(57) ABSTRACT

A flexible, sterilizable pouch includes a first wall coupled to a second wall and a cavity defined between the first wall and the second wall. The cavity is configured to receive a medical device, and the pouch is configured to seal the medical device within the cavity. At least one of the first wall and the second wall of the pouch includes two layers. Each layer is coupled to the adjacent layer such that a breach in any one layer of the multi-layered wall will not breach the seal of the pouch. A pocket may be formed between the layers of the multi-layered wall and may include a gas under pressure to inflate the corresponding wall to an inflated state.

17 Claims, 15 Drawing Sheets

(56) References Cited

U.S. PATENT DOCUMENTS

| | | | |
|---|---|---|---|
| 4,660,721 A | 4/1987 | Mykleby | |
| 5,263,587 A * | 11/1993 | Elkin | B65D 81/052 206/522 |
| 5,564,570 A * | 10/1996 | Jaszai | B65D 81/1075 206/213.1 |
| 5,647,480 A * | 7/1997 | Insley | B65D 33/20 206/204 |
| 5,653,090 A | 8/1997 | Weiss et al. | |
| 5,791,476 A * | 8/1998 | Stekloff | B65D 31/12 206/521 |
| 5,947,287 A | 9/1999 | Weiss et al. | |
| 6,251,489 B1 | 6/2001 | Weiss et al. | |
| 7,066,331 B2 * | 6/2006 | Koyanagi | B65D 81/052 206/522 |
| 8,123,035 B2 * | 2/2012 | Won | B65D 81/03 206/522 |
| 2005/0268573 A1 | 12/2005 | Yan | |
| 2009/0169134 A1 * | 7/2009 | Hsu | H65D 81/03 383/3 |
| 2011/0192121 A1 * | 8/2011 | Kannankeril | B65B 55/20 53/473 |
| 2014/0133785 A1 | 5/2014 | Diviesti et al. | |
| 2015/0314940 A1 * | 11/2015 | Matta | B65D 75/58 206/522 |
| 2019/0016518 A1 * | 1/2019 | Cheich | B31D 5/0073 |

FOREIGN PATENT DOCUMENTS

| | | |
|---|---|---|
| EP | 0 306 207 A1 | 3/1989 |
| WO | 96/39340 A1 | 12/1996 |

OTHER PUBLICATIONS

Written Opinion dated Jan. 4, 2018 in corresponding International Patent Application No. PCT/US2017/053656.

* cited by examiner

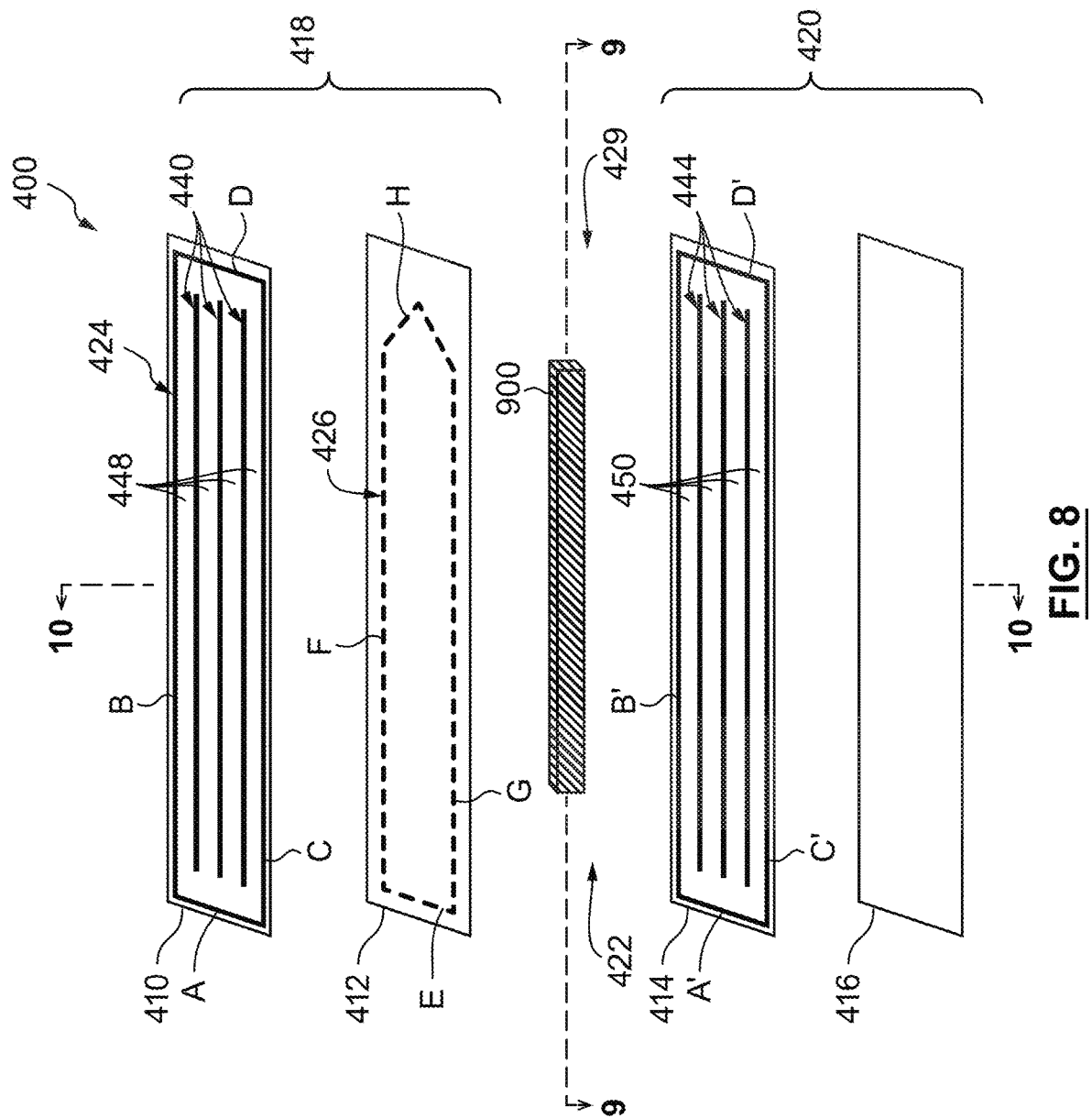

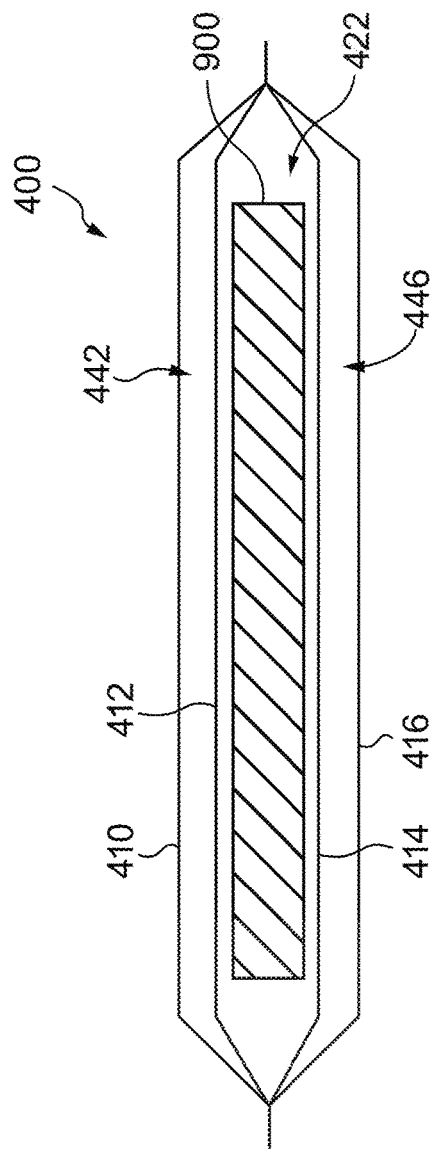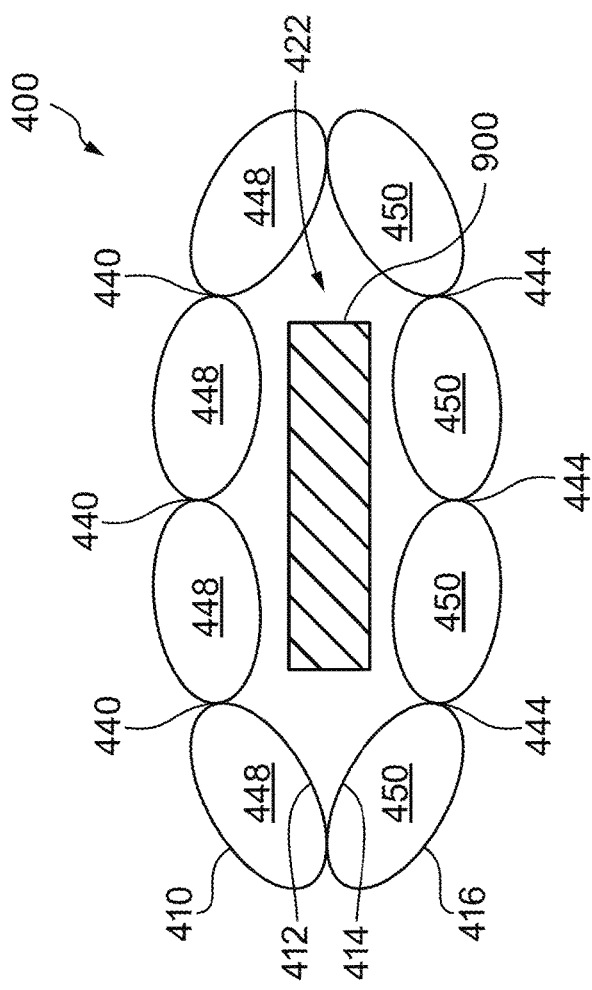

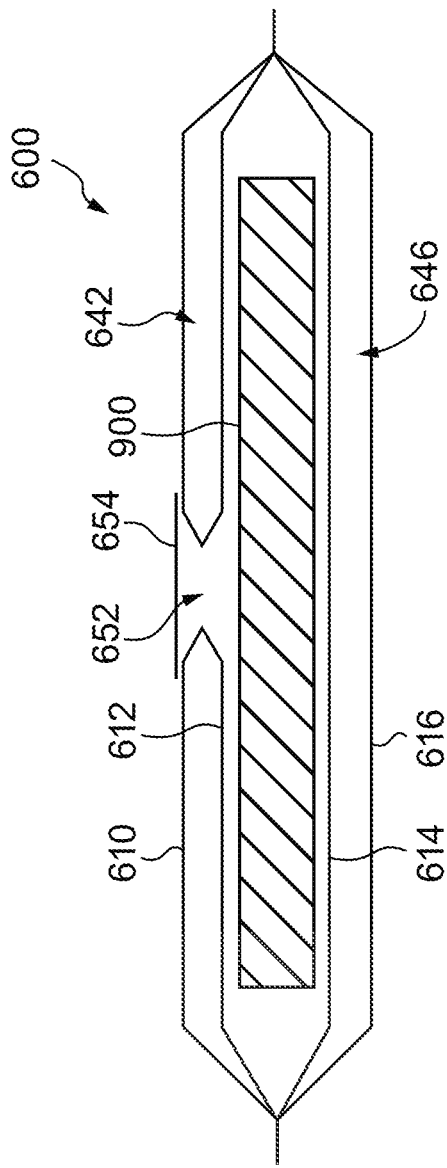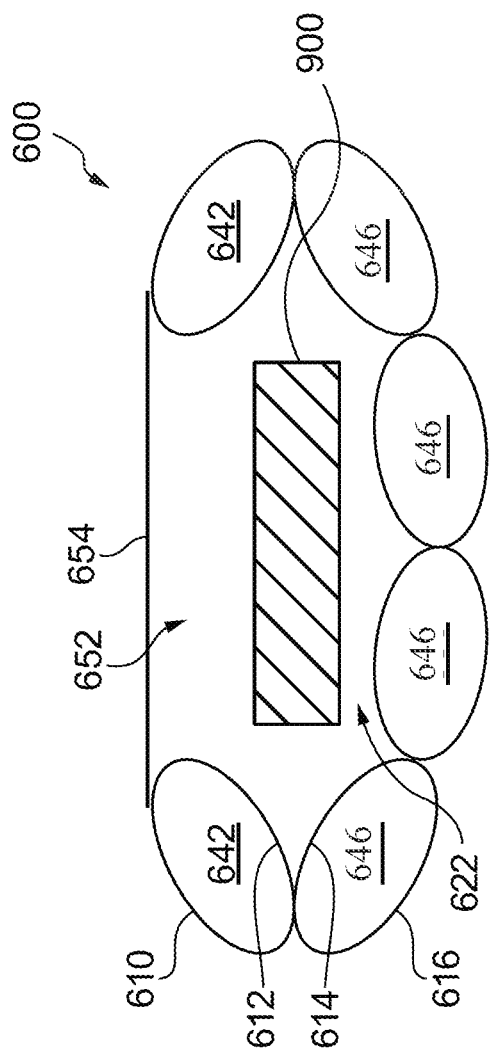

POUCHES WITH MULTI-LAYER WALLS FOR IMPROVED DURABILITY AND PROTECTION OF MEDICAL DEVICES

CROSS REFERENCE TO RELATED APPLICATIONS

This application is a divisional of U.S. patent application Ser. No. 15/716,859, filed Sep. 27, 2017, which claims the benefit under 35 U.S.C. § 119(e) of the filing date of U.S. Provisional Application No. 62/400,205 filed Sep. 27, 2016, the contents of each of which are incorporated by reference herein, in their entirety.

FIELD OF THE INVENTION

The present invention relates to sterilizable, flexible medical device pouches. More particularly, the present invention relates to medical device pouches with multi-layer walls for improved durability and protection.

BACKGROUND OF THE INVENTION

Sterilizable, flexible pouches, hereafter referred to as pouches, for maintaining the sterility of objects, such as medical devices, for surgical applications have been utilized for many years. Such pouches typically utilize a bag fabricated from flexible, non-porous plastics such as polyethylene and/or gas-permeable materials such as a DuPont product called Tyvek®. Sterilization is accomplished after sealing the medical device within the pouch by exposing the sealed pouch to, for example, a sterilization gas such as ethylene oxide (EtO) or steam, or radiation such as an electron beam or gamma radiation.

In an example, a pouch may utilize a gas-permeable membrane as a first layer of the pouch. The gas-permeable layer is peelably adhered to a second layer of the pouch. When the medical device stored therein is to be removed, the first layer is separated or peeled from the second layer and the medical device removed.

Sterilizable pouches are generally formed from a continuous strip or strips of materials on an intermittent feed heat sealing machine. An opening to access the pouch is left unsealed such that a medical device may be placed therein. Once the medical device is placed within the pouch, the opening is sealed with a heat sealing machine and the pouch and the medical device are sterilized with a selected sterilization process.

These pouches offer sterile presentation and opening in a small footprint. Additionally, the pouches are low cost, easy to handle, and readily disposable. However, these pouches are not particular durable and may fail during transport, handling, and/or storage. More specifically, a breach, or hole may form in a layer of the pouch, sometimes due to a shipping carton rubbing against the pouch during transport. Alternatively, the medical device stored within the pouch may rub against the layers of the pouch form the inside and cause a breach. Any breach in a layer of the single layer pouch renders the medical device therein unsterile and not suitable for immediate service.

Moreover, the current pouches afford the medical device stored within only minimal protection from damage during transportation, handling and storage. Accordingly, there is a need for sterilizable, flexible medical device pouches with improved durability. There is also a need for sterilizable, flexible medical device pouches that afford better protection to enclosed medical devices.

BRIEF SUMMARY OF THE INVENTION

Embodiments here of relate to a flexible, sterilizable pouch including a first wall, a second wall coupled to the first wall, and a cavity defined between the coupled first wall and second wall. The cavity is configured to receive a medical device, and the pouch is configured to seal the medical device within the cavity. At least one of the first wall and the second wall includes more than one layer, with each layer coupled to the adjacent layer. A breach in any one layer of the multi-layered first wall or second wall will not breach the seal of the pouch.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 8 depicts an exploded perspective view of a pouch in accordance with another embodiment hereof, wherein the pouch includes a pocket configured to receive a gas.

FIG. 9 depicts a longitudinal cross-sectional view of the pouch taken at line 9-9 of FIG. 8 with the pouch sealed.

FIG. 10 depicts a cross-sectional view of the pouch taken at line 10-10 of FIG. 8 with the pouch sealed.

FIG. 15 depicts a longitudinal cross-sectional view of the pouch taken at line 15-15 of FIG. 14 with the pouch sealed.

FIG. 16 depicts a cross-sectional view of the pouch taken at line 16-16 of FIG. 14 with the pouch sealed.

DETAILED DESCRIPTION OF THE INVENTION

Specific embodiments of the present invention are now described with reference to the figures, wherein like reference numbers indicate identical or functionally similar elements.

The following detailed description is merely exemplary in nature and is not intended to limit the invention or the application and uses of the invention. Although the description of embodiments hereof is in the context of pouches used for sterilization, storage and transportation of medical devices, pouches described herein can also be used in other applications and for other devices. Furthermore, there is no intention to be bound by any expressed or implied theory presented in the preceding technical field, background, brief summary or the following detailed description.

Embodiments of the present invention disclose a multi-layer, sterilizable, and flexible medical device pouch (hereafter referred to as a "pouch") also referred to as a bag, receptacle, or compartment, with improved durability. Embodiments hereof further disclose pouches with improved protection of the medical devices stored therein. The pouches may be configured to specific medical device products needs to improve the robustness of the component and ensure sterility is not compromised through testing and hence in the field.

Figure 1:
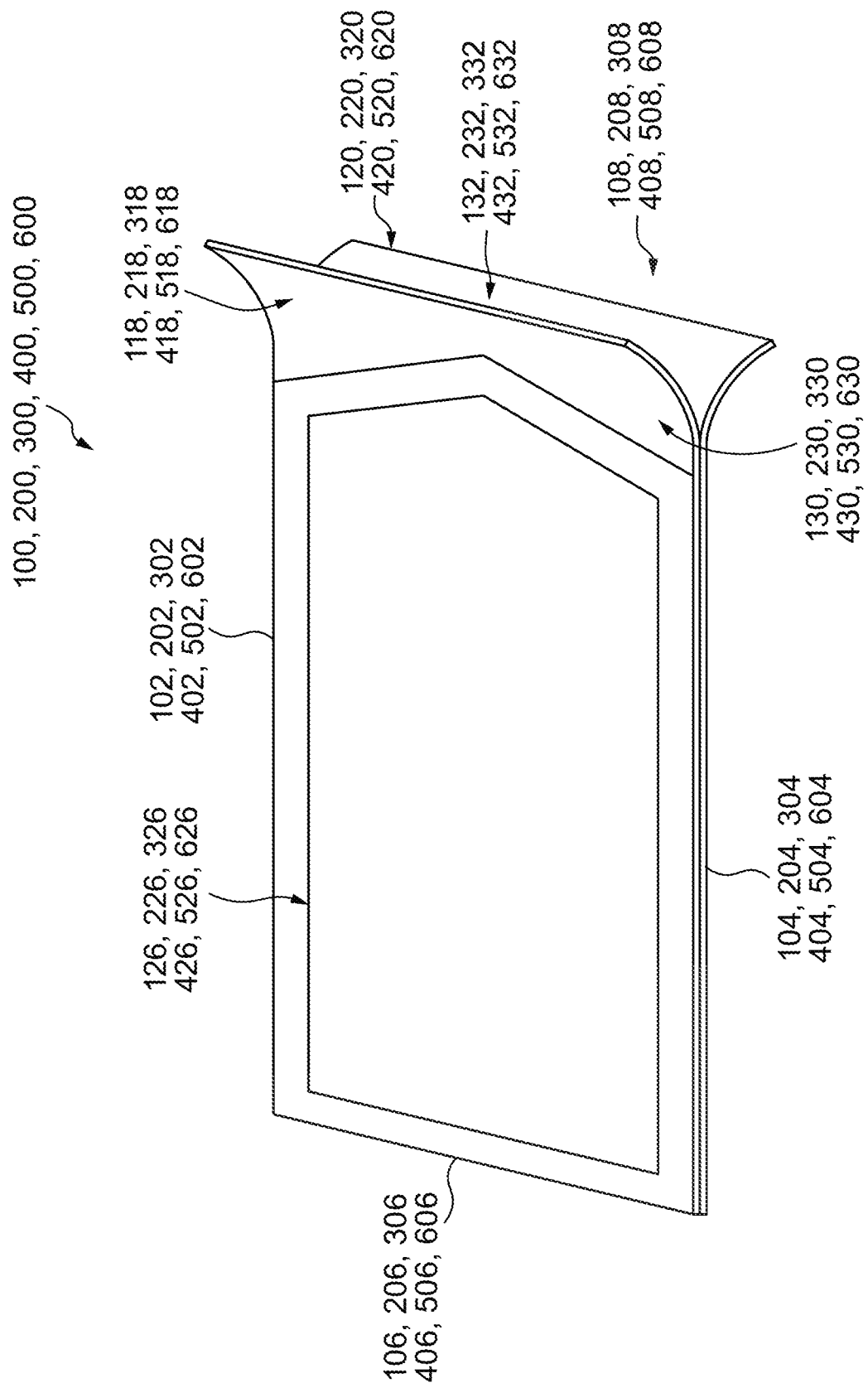
FIG. 1 depicts a planar view of a pouch with a multi-layer wall in accordance with embodiments hereof.
Figure 2:
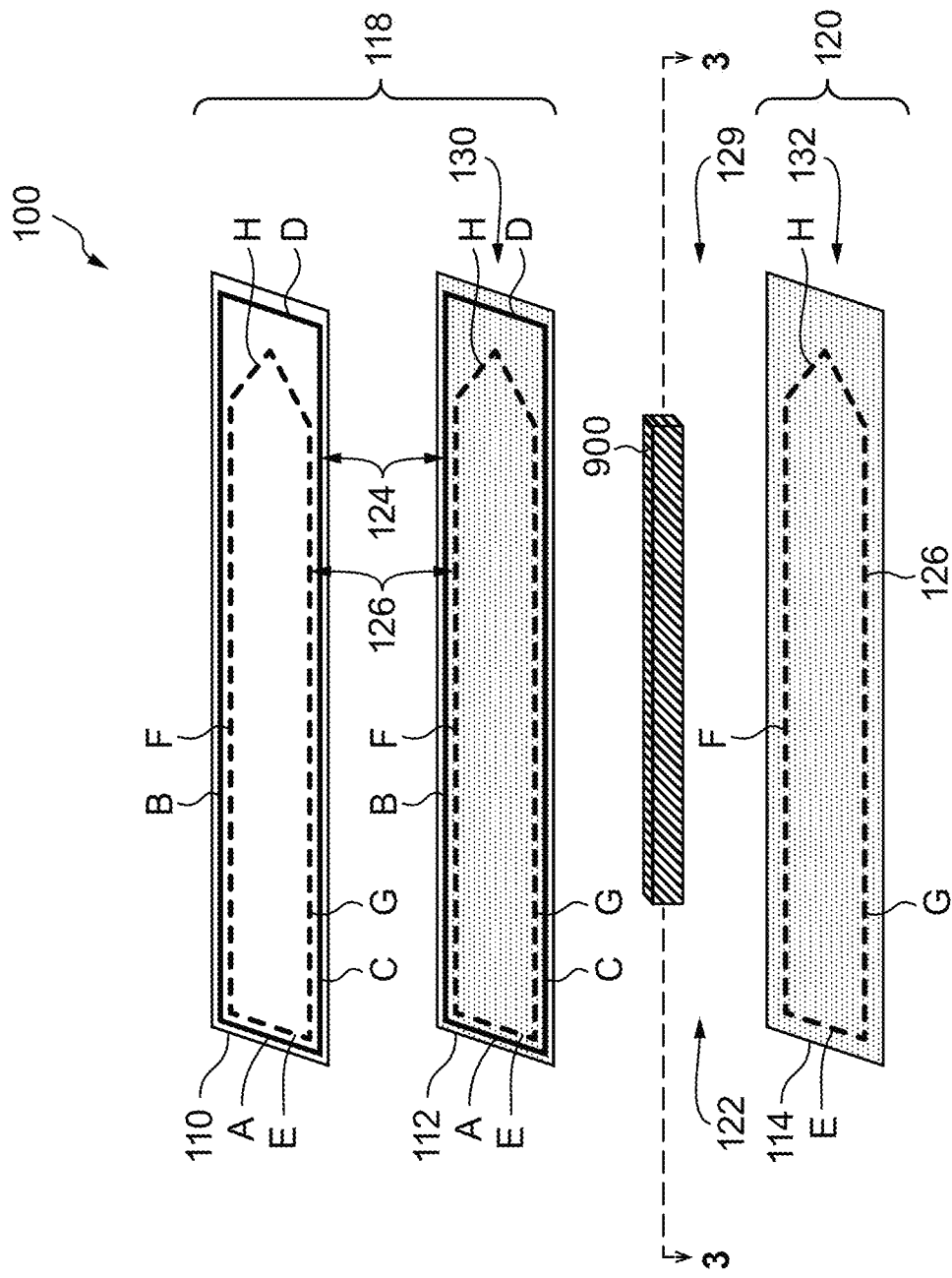
FIG. 2 depicts an exploded perspective view of an embodiment of the pouch of FIG. 1.
Figure 3:
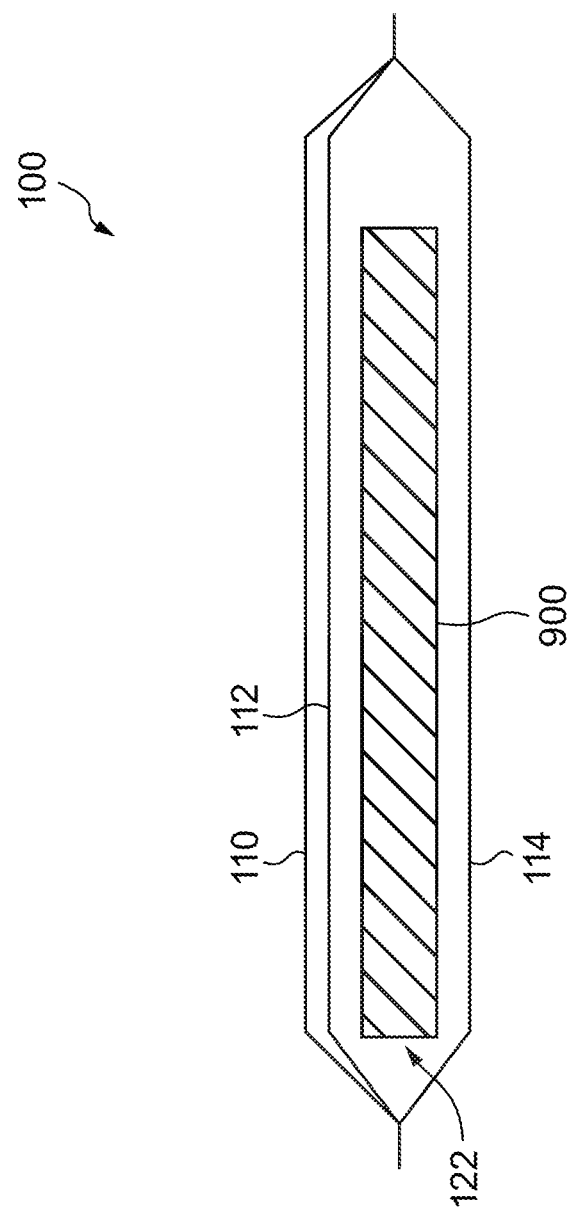
FIG. 3 depicts a longitudinal cross-sectional view of the pouch taken at line 3-3 of FIG. 2 with the pouch sealed.

A pouch 100 in accordance with an embodiment hereof is shown in FIGS. 1-3. The pouch 100 includes a first edge 102, a second edge 104 opposite the first edge 102, a third edge 106, and a fourth edge 108 opposite the third edge 106, as shown in FIG. 1. The pouch 100 further includes a first wall 118 and a second wall 120, as shown in FIGS. 2-3. A cavity 122 is defined between the first wall 118 and the second wall 120, as described below. The cavity 122 is configured to receive an object, such as a medical device 900, therein, as shown in FIG. 3. The pouch 100 is configured to seal the medical device 900 within the cavity 122 as described below.

In the embodiment of FIGS. 1-3, the first wall 118 includes a first layer or web 110, and a second layer 112. As used herein the term "layer" or "web" means a formed sheet that may be a laminate of several layers formed together. Thus, a laminate with several materials formed together as a single sheet is a single layer, not more than one layer, as would be understood by those skilled in the art. The first layer 110 is coupled to the second layer 112 at a first seal 124 in the regions A, B, C, and D to form the first wall 118, as shown in FIG. 2. The first and second layers 110 may be sealed to each other by using pressure combined with heat creating a welded or peelable seal. The regions A, B, C, and D, as used herein to describe locations where two layers of a wall are attached to each other is intended to such that the first seal 124 extends to the edges of each layer. In such a manner, the first wall 118 presents itself to a user as a single layer, rather than as two layers. This prevents a user from peeling the first and second layers 110, 112 apart rather than peeling the first and second walls 118, 120 apart, as described in more detail below. Further, it is preferable that regions away from regions A, B, C, and D of the first and second layers 110, 112 are not attached to each other to permit relative movement between the first and second layers.

The second wall 120 includes a single, third layer 114. The first wall 118 is coupled to the second wall 120 at a second seal 126 in regions E, F, G, and H. The regions E, F, G, and H, as used herein to describe where two walls are attached to each other is intended to include regions both at the edges of walls as well as to regions that are near the edges of the walls. The second seal 126 may be accomplished via heat sealing such as by using pressure combined with heat to create a welded or peelable seal.

In the embodiment of FIGS. 1-3, the first layer 110 is formed of a gas-impermeable film or foil material, such as, but not limited to aluminum, low-density polyethylene (LDPE), nylon, or polyester. The first layer 110 provides an effective barrier against the migration of micro-organisms, including bacteria. The material of the first layer 110 is selected such that the first layer 110 may be sealed with the second layer 124 along the first seal 124.

In the embodiment of FIGS. 1-3, the second layer 112 and the third layer 114 are each formed of a gas-permeable material such as, but not limited to a spun-bonded polyolefin marketed by DuPont under the name Tyvek® or medical grade paper. The second and third layers 112, 114 each permit sterilization of the pouch 100 and the medical device 900 disposed within the cavity 122 by methods such as, but not limited to ethylene oxide gas (EtO), steam sterilization, or other suitable sterilization methods using a temperature at or below 260° F. Further, the second and third layers 112, 114 each provide an effect barrier against migration of micro-organisms, particularly bacteria. The material of the second layer 112 is selected such that it can be sealed to the first layer 110 along first seal 124. The materials of the first, second, and third layers are selected such that they can be sealed along second seal 126.

The pouch 100 is assembled by superposing the first layer 110 over the second layer 112 and subjecting the first layer 110 and the second layer 112 to a sealing process such that the first seal 124 is formed in the regions A, B, C, and D between the first layer 110 and the second layer 112. Formation of the first seal 124 couples the first layer 110 to the second layer 112 to form the first wall 118.

The first wall 118 is superposed over the second wall 120, in this embodiment the single, third layer 114, and subjected to a sealing process to form the second seal 126 in the regions E, F, and G to couple the first wall 118 to the second wall 120.

The second seal 126 defines the outer limits of the cavity 122. As noted above, at this point in the manufacture of the pouch 100, the only three sides of the second seal 126 (regions E, F, and G) between the first wall 118 and the second wall 120 have been formed. In order to permit the placement of a medical device, such as the medical device 900 within the cavity 122, the second seal 126 between the first wall 118 and the second wall 120 is omitted from the region H. Thus, an opening 129 between the first and second walls 118, 120 to the cavity 122 is provided at region H. In the embodiment of FIGS. 1-3, the opening 129 is provided at the fourth edge 108 of the pouch 100, but the opening 129 may be formed along any of the edges. While shown in FIG. 2 with the opening 129 extending generally fully across the length of the fourth edge 108, this is by way of example and not limitation, and the opening 129 may extend for a lesser distance. The medical device 900 may then be placed within the cavity 122. The pouch 100 is subjected to another sealing process to form the second seal 126 in the region H to seal the medical device 900 within the cavity 122.

The second seal 126 at region H may be formed at a different location/time than the other regions. For example, and not by way of limitation, a pouch manufacturer may provide the pouch 100 with the first seal 124 at regions A, B, C, and D, and the second seal 126 at regions E, F, and G. The pouch manufacturer may ship the pouch 100 to a medical device manufacturer. The medical device manufacturer may insert the medical device 900 into the cavity 122 and provide the second seal 126 at the region H. Alternatively, the medical device manufacturer may ship the medical device to the pouch manufacturer who inserts the medical device 900 into the cavity 122 and provides the second seal 126 at the region H. Other combinations may also be used, such as a third party receiving both the pouch 100 and the medical device 900, inserting the medical device 900 into the pouch 100, and then providing the second seal at region H.

The pouch 100 may next be sterilized using any suitable method, such as, but not limited to exposure to ethylene oxide (EtO), electron beam radiation, gamma radiation, or steam at or below 260° F. for a requisite duration to ensure sterility of the pouch 100 and the medical device 900 disposed therein. When the package 100 and the medical device 900 disposed therein has been adequately sterilized, the package 100 may be placed within a shipping carton or container for transport, storage, and handling, When it is desired to use the medical device 100, the medical device needs to be removed from the pouch 100. In the embodiment shown in FIG. 1-3, the second seal 126 between the first wall 118 and the second wall 120 at region H is spaced from the fourth edge 108, thereby creating a first flange 130 in the first wall 118 and a second flange 132 in the second wall 120, as shown in FIG. 1. The pouch 100 is opened by grasping the first flange 130 and the second flange 132, and pulling the first and second flanges 130, 132 apart. Although the first and second flanges 130, 132 are described at fourth edge 108, wherever second seal 126 is spaced from one of the edges of the pouch 100, respective flanges are formed which may be used to open the pouch 100. As explained above, it is preferable that the first seal 124 (between first and second layers 110, 112) at regions A, B, C, and D is disposed at the edges of the first and second layers 110, 112 such that the first and second layers 110, 112 appear as a single layer to the user. This prevents the user from separating the first and second layers 110, 112 from each other, rather than the first and second walls 118, 120 from each other. However, if the second seal 126 is disposed at the first, second, and third edges 102, 104, 106, then the first seal 124 between the first and second layers 110, 112 may only need to be disposed at the edges of the first and second layers 110, 112 at region D (fourth edge 108).

As briefly explained above, portions of the first and second layers 110, 112 of the first wall 118 may move independent of each other between the regions of the first seal 124. With the independent movement, the likelihood of a breach or hole in both the first layer 110 and the second layer 112 is lessened or reduced by the redundancy of the double-layer construction of the first wall 118 and the independent movement of the first layer 110 and the second layer 112 of the first wall 118. More specifically, when the medical device 900 is disposed within the cavity 122, the medical device 900 is adjacent to and in contact with only the second layer 112. Thus, movement of the medical device 900 relative to the second layer 112 may wear the second layer 112, but will not contact, and therefore will not rub, wear, or breach the first layer 110 until after the second layer 112 has been breached. Conversely, when the pouch 100 is placed in a shipping carton for transport, handling, or storage, the first layer 110 is adjacent to and in contact with the carton. Movement of the pouch 100 relative to the carton may wear the first layer 110, but will not contact, and therefore will not rub, wear, or breach the second layer 112 until after the first layer 112 has been breached. Thus, a breach in any one layer of the multi-layer first wall 118 will not compromise the sterility of the medical device 900, thereby improving the durability of the pouch 100.

Figure 4:
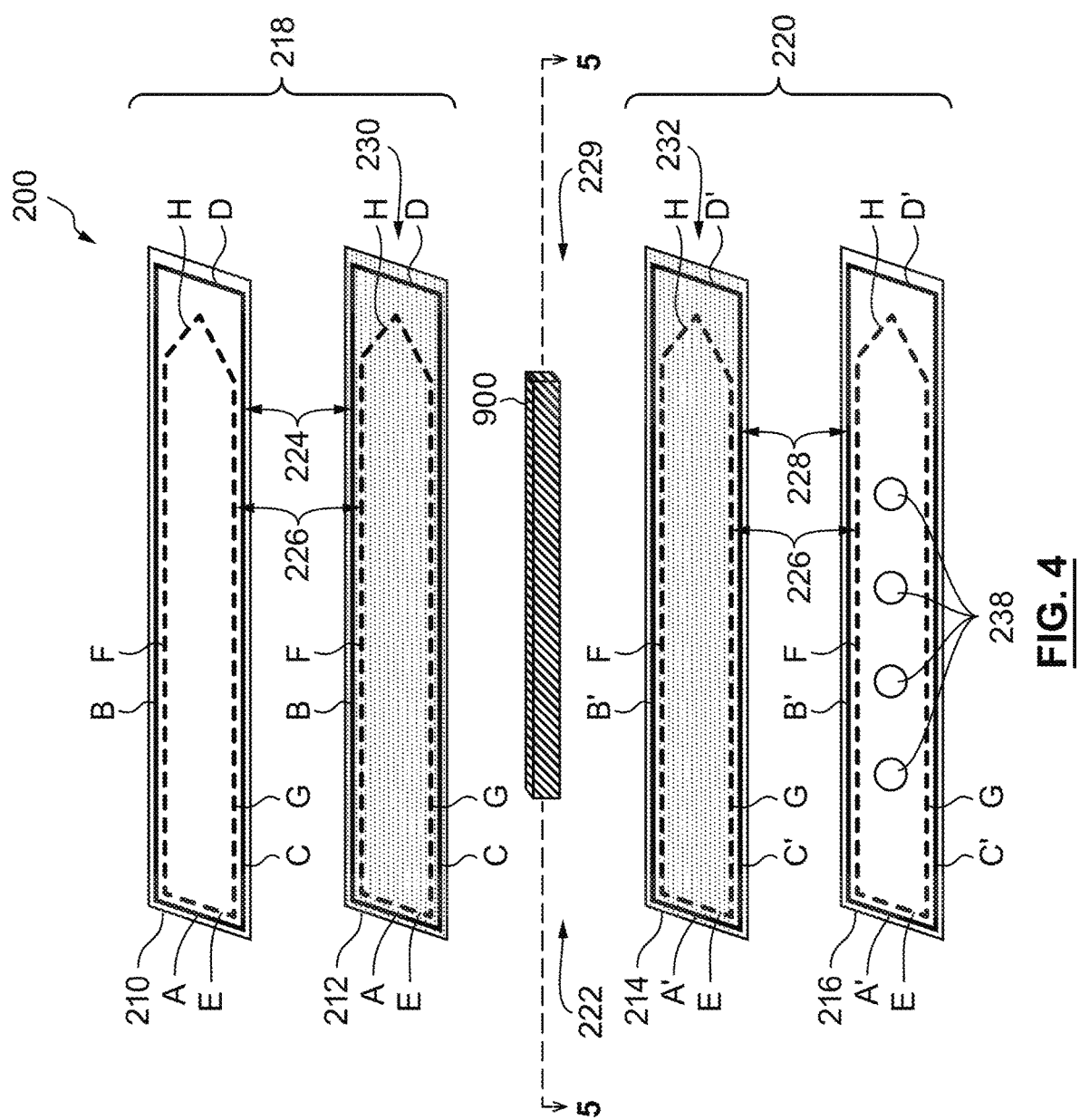
FIG. 4 depicts an exploded perspective view of a pouch in accordance with another embodiment hereof.
Figure 5:
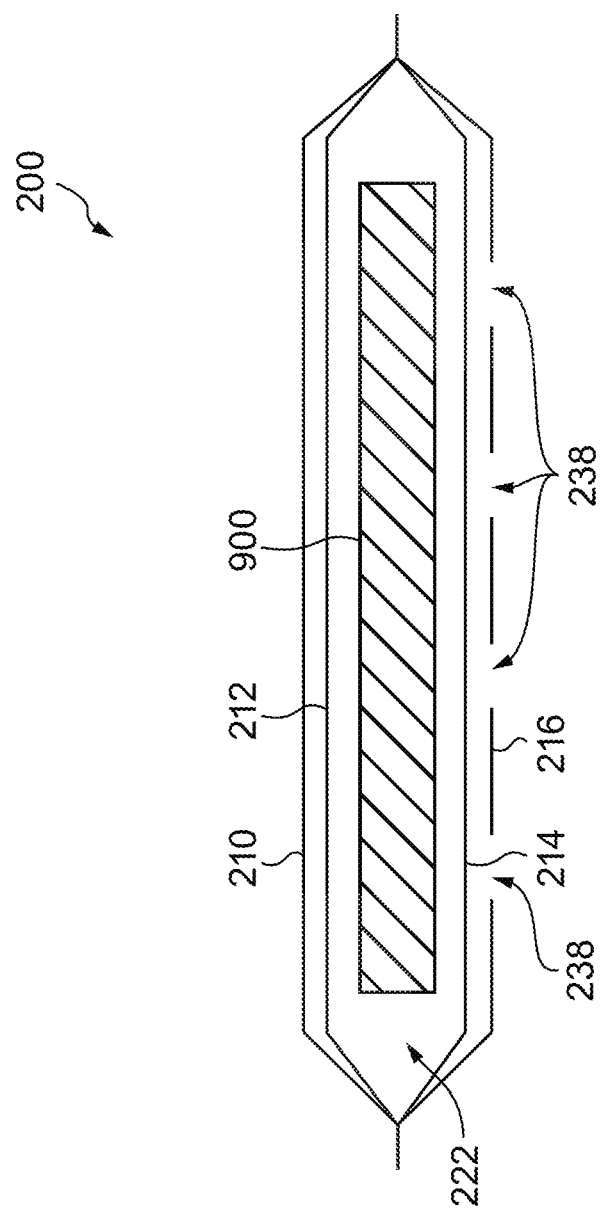
FIG. 5 depicts a longitudinal cross-sectional view of the pouch taken at line 5-5 of FIG. 4 with the pouch sealed.

FIGS. 1 and 4-5 show a pouch 200 in accordance with another embodiment hereof. The pouch 200 includes a first edge 202, a second edge 204, a third edge 206, a fourth edge 208, a first layer 210, a second layer 212, a third layer 214, a first wall 218, a second wall 220, a cavity 222, a first seal 224, a second seal 226, a first flange 230, and a second flange 232 that are similar to the similarly numbered items of the pouch 100. Therefore, a detailed explanation of the construction and alternatives of these similar components will not be described. However, the second wall 220 of the pouch 200 further includes a fourth layer 216.

In the embodiment of FIGS. 4-5, the second wall 220 includes the third layer 214 coupled to the fourth layer 216 by a third seal 228 in the regions A', B', C', and D', as shown in FIG. 4. The cavity 222 is defined between the first wall 218 and the second wall 220.

The first layer 210, the second layer 212, and the third layer 214 are formed of materials as described previously with respect to same layers of the pouch 100 of FIGS. 1-3. The fourth layer 216 is formed of a gas-impermeable film or foil material, such as, but not limited to aluminum, low-density polyethylene (LDPE), nylon, or polyester. The fourth layer 216 may be formed of the same material as the first layer 210. The material of the fourth layer 216 is selected such that it may be sealed to the third layer 214 and the third seal 228 and such that it may be sealed with the first, second, and third layers by the second seal 226.

The fourth layer 216 includes a plurality of perforations 238. The plurality of perforations 238 are apertures or openings through the fourth layer 216. The plurality of perforations 238 permit gas to pass through the fourth layer 216 such that sterilization passes through the perforations 238, the third layer 214, into the cavity 222, and through the second layer 212. The plurality of perforations 238 may be disposed at any location of the fourth layer 216 within the area defined by third seal 228. However, it is preferred that no perforation 238 is located adjacent to any sharp edges, ends or protrusions of a medical device 900 disposed within the pouch 200. While the plurality of perforations 238 are shown in FIGS. 4-5 with a circular shape, it will be understood that this is by way of example and not limitation, and the plurality of perforations 238 may have other shapes including but not limited to ovals, rectangles, or other suitable shapes. Moreover, each perforation 238 may have the same, or different shape than another perforation 238 in any combination. Even further, while the fourth layer 216 is shown with a specific number of perforations 238, this too is by way of example and not limitation, and the fourth layer 216 may have a greater or fewer number of perforations 238.

Assembly of the pouch 200 is similar to the assembly of the pouch 100 of FIGS. 1-3. The first wall 218 is formed as described previously with respect to the first wall 118 of FIGS. 1-3. The second wall 220 is assembled by superposing the third layer 214 over the fourth layer 216 and subjecting the third and fourth layers 214, 216 to a sealing process such that the third seal 228 is formed in the regions A', B', C', and D' between the third layer 214 and the fourth layer 216. The first wall 218 is then superposed over the second wall 220 and subjected to a sealing process to form the second seal 226 in the regions E, F, and G, as previously described with respect to the pouch 100 of FIGS. 1-3.

When the pouch 200 has been assembled, the medical device 900 disposed within the cavity 222 through an opening 229 adjacent the fourth edge 208. Next, the pouch 200 is subjected to another sealing process to form the second seal 226 in the region H to seal the medical device 900 within the cavity 222 of the pouch 200.

The pouch 200 may next be sterilized using any suitable method, such as, but not limited to exposure to ethylene oxide (Eta), electron beam radiation, gamma radiation, or steam at or below 260° F. for a requisite duration to ensure sterility. The perforations 238 in the fourth layer 216 permit the use of gas sterilization methods, as the sterilization gas may pass through the perforations 238 in the impermeable fourth layer 216 and then proceed through the gas-permeable third and second layers 214, 212 and into the cavity 222.

The additional fourth layer 216 of the second wall 220 means the likelihood of a breach in both the fourth layer 216 and the adjacent third layer 214 is reduced. Similar to the embodiment of FIGS. 1-3, the portions of the third layer 214 and the fourth layer may move relative to each other in the areas not sealed by third seal 228. When the medical device 900 is disposed within the cavity 222, the medical device 900 is adjacent to and in contact with only the third layer 214. Movement of the medical device 900 relative to the third layer 214 will wear the third layer 214, but will not contact, rub, wear, or breach the fourth layer 216 until after the third layer 214 has been breached. Conversely, when the pouch 100 is placed in a shipping carton for transport, handling, and storage, the fourth layer 216 is adjacent to and in contact with the carton, and movement of the pouch 200 relative to the carton will wear the fourth layer 216, but will not contact, rub, wear, or breach the third layer 214 until after the fourth layer 216 has been breached. A breach in any one layer of the multi-layer first wall 118 or the multi-layer second wall 220 will not compromise the sterility of the medical device 900.

Opening of the pouch 200 is similar to the opening of the pouch 100 described previously with respect to FIGS. 1-3. In the embodiment shown in FIGS. 1 and 4-5, the second seal 226 between the first wall 218 and the second wall 220 at region H is spaced from the fourth edge 208, thereby creating a first flange 230 in the first wall 118 and a second flange 232 in the second wall 220, as shown in FIG. 1. The pouch 200 is opened by grasping the first flange 230 and the second flange 232, and pulling the first and second flanges 230, 232 apart.

Figure 6:
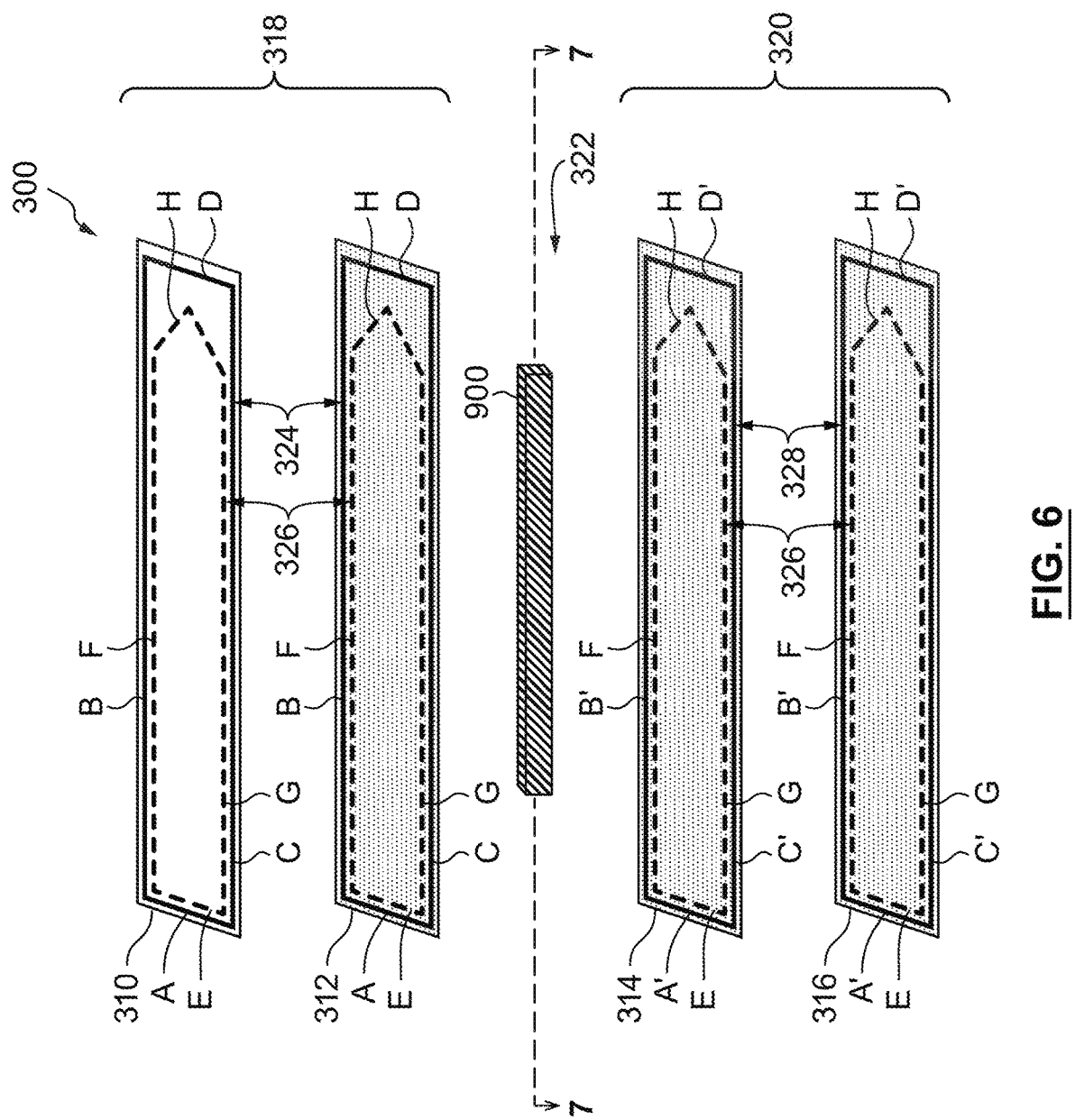
FIG. 6 depicts an exploded perspective view of a pouch in accordance with another embodiment hereof.
Figure 7:
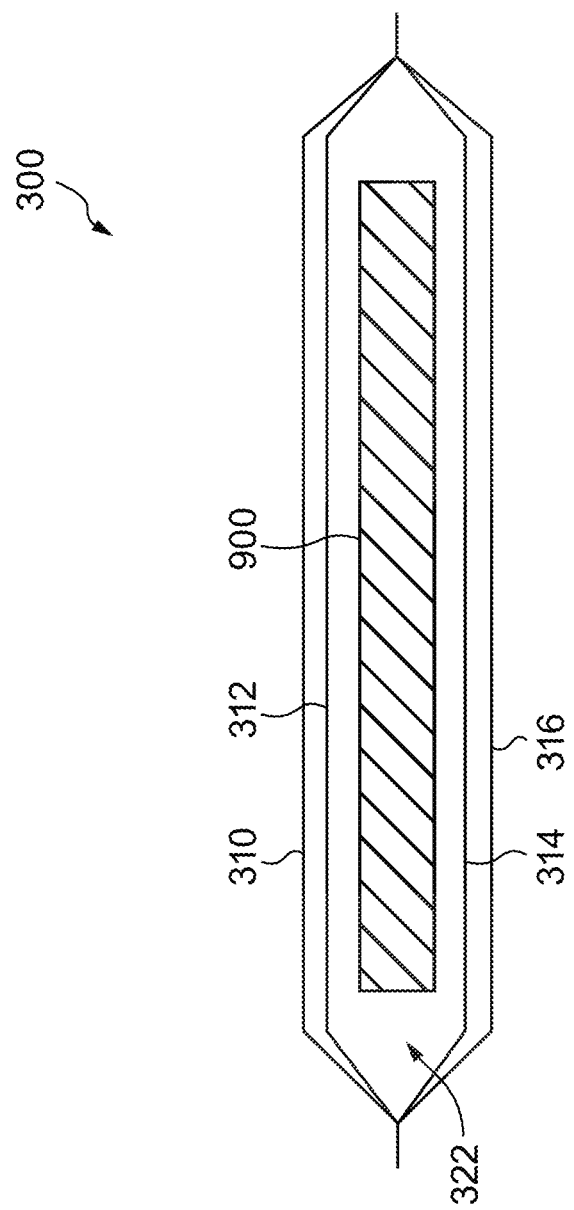
FIG. 7 depicts a longitudinal cross-sectional view of the pouch taken at line 7-7 of FIG. 6 with the pouch sealed.

A pouch 300 in accordance with another embodiment hereof is shown in FIGS. 1 and 6-7. The pouch 300 includes a first edge 302, a second edge 304, a third edge 306, a fourth edge 308, a first layer 310, a second layer 312, a third layer 314, a fourth layer 316, a first wall 318, a second wall 320, a cavity 322, a first seal 324, a second seal 326, a third seal 328, a first flange 330, and a second flange 332. The pouch 300 and its components are similar that are similar to the similarly numbered items of the pouch 200. Therefore, a detailed explanation of the construction and alternatives of these similar components will not be described. However, in contrast to the fourth layer 216 of the pouch 200, the fourth layer 316 of the pouch 300 is formed of a gas-permeable material such as, but not limited to a spun-bonded polyolefin marketed by DuPont under the name Tyvek® or medical grade paper. Accordingly, the fourth layer 316 does not include perforations because it is gas-permeable. The pouch 300 is constructed in the same manner as the pouch 200 described above, and provides improved durability with a multi-layer configuration for both the first wall 318 and the second wall 320, as described with respect to the pouch 200 of FIGS. 1 and 4-5.

FIGS. 1 and 8-10 show a pouch 400 in accordance with another embodiment of the present disclosure. The pouch 400 includes a first edge 402, a second edge 404, a third edge 406, a fourth edge 408, a first layer 410, a second layer 412, a third layer 414, a fourth layer 416, a first wall 418, a second wall 420, a cavity 422, a first seal 424, a second seal 426, a third seal 428, a first flange 430, and a second flange 432. These components of pouch 400 are similar to the similarly numbered items of the pouch 200. Therefore, a detailed explanation of the construction and alternatives of these similar components will not be described. However, in the embodiment of FIGS. 8-10, both the first and second layers 410, 412 of the first wall are formed from a gas-impermeable material, and both the third and fourth layers 414, 416 of the second wall 420 are formed from a gas-impermeable material. Further, the first wall 418 includes a pocket 442 between the first and second layers 410, 412, and the second wall 420 includes a pocket 446 between the second and third layers 414, 416. Further, the pockets 442 and 446 each has an inflated state.

In the embodiment of FIGS. 8-10, the first layer 410, the second layer 412, the third layer 414, and the fourth layer 416 are each formed of a gas-impermeable film or foil material, such as, but not limited to aluminum, low-density polyethylene (LDPE), nylon, or polyester.

The first wall 418 includes the first layer 410 coupled to the second layer 412 by a first seal 424 in the regions A, B, C, and D, and a plurality of fourth seals 440. The pocket 442 is formed between the first and second layers 410, 412 and the first and fourth seals 424, 440, as shown in FIG. 8. The first wall 418 is configured to receive a gas under pressure into the pocket 442 to transition the first wall 418 from an uninflated state to and inflated state, as best shown in FIG. 10. When in the inflated state, the first wall 418 is configured to protect a medical device 900 disposed within the cavity 422 of the pouch 400 from damage.

Similarly, the second wall 420 includes the third layer 414 coupled to the fourth layer 416 by the second seal 426 in the regions A', B', C', and D', and a plurality of fifth seals 444. The pocket 446 is formed between the third and fourth layers 414, 416 and the second and fifth seals 426, 444, as shown in FIG. 8. The second wall 420 is configured to receive a gas under pressure into the pocket 446 to transition the second wall 420 from an uninflated state to the inflated state, as shown in FIG. 10. When in the inflated state, the second wall 420 is configured to protect the medical device 900 disposed within the cavity 422 of the pouch 400, as described below.

To assemble the pouch 400, the first layer 410 is superposed over the second layer 412, and the first layer 410 and the second layer 412 are subjected to a sealing process such that the first seal 424 is formed in the regions A, B, C, and D and the plurality of fourth seals 440 are formed between the first layer 410 and the second layer 412 to couple the first layer 410 to the second layer 412. A gas under pressure is provided to the pocket 442 of the first wall 418 to inflate the wall 418. The gas flows within the pocket 442 and around the plurality of fourth seals 440 to form a plurality of interconnected cushions, pillows or bubbles 448, as shown in FIG. 10. The firmness of the plurality of cushions 448 may be adjusted through adjustment of the gas pressure during the sealing process to customize each pouch 400 for a specific medical device. Similarly, the third layer 414 is coupled to the fourth layer 416 by superposing the third layer 414 over the fourth layer 416 and subjecting the third layer 414 and the fourth layer 416 to a sealing process. The sealing process forms the third seal 428 in the marginal regions A', B', C', and D' and the plurality of fifth seals 444 between the third layer 414 and the fourth layer 416 of the second wall 420. During the sealing process, a gas under pressure is provided to the pocket 446 to form the second wall 420 in the inflated state. The gas flows within the pocket 446 and around the plurality of fifth seals 442 to form a plurality of interconnected cushions, pillows or bubbles 450.

The first wall 418 in the inflated state is superimposed over the second wall 420 in the inflated state and subjected to a sealing process to form the second seal 426 in the marginal regions E, F, and G. Formation of the second seal 426 couples the first wall 418 to the second wall 420 and forms the cavity 422 between the first wall 418 and the second wall 420.

When the pouch 400 has been assembled to this point, the medical device 900 may be disposed through an opening 429 and received within the cavity 422. The pouch 400 is then subjected to a sealing process to form the second seal 426 in the marginal region H, thereby sealing the medical device 900 within the cavity 422. The pouch 200 may next be sterilized using any suitable method that does not require a gas pathway, such as, but not limited to exposure to electron beam radiation or gamma radiation to ensure sterility.

It is noted that in FIG. 8, the seal lines are shown in only some of the layers for clarity. Thus, the first seal 424 and the fourth seals 440 are shown only in the first layer 410, but they extend to both the first layer 410 and the second layer 412 to couple them together. Similarly, the third seal 428 and the fifth seals 444 are shown only in the third layer 414, but they extend to both the third layer 414 and the fourth layer 416. Similarly, the second seal 426 is shown only in the second layer 412, but it extends to the first, second, third, and fourth layers 410, 412, 414, and 416.

The multiple layers of the first wall 418 and the second wall 420 each reduce the likelihood of a breach in the corresponding wall, as described previously with respect to the embodiments of pouches 100, 200, and 300 of FIGS. 1-7. Further the cushions 448, 450 of the first and second walls 418, 420 in the inflated state provide protection to the medical device 900 stored within the pouch 400, particularly in potentially high-impact areas. The gas-filled pockets 442, 446 of the first and second walls 418, 420, and more specifically, the cushions 448, 450 of the first and second walls 418, 420, are each configured to protect to the medical device 900 disposed therein from damage occurring during transportation, storage, and/or handling of the pouch 400 to insure the medical device 900 is delivered in good, usable, and sterile condition.

It will be understood that the shape of the cushions of each wall of the pouch 400 may be designed to fit snugly within a shipping carton or container to minimize or reduce folding or movement of the pouch 400. The shape of the cushions of each wall may further be designed such that the medical device 900 may sit on the cushion, the cushion may surround the medical device 900, or a combination thereof. The shape of the cushions may be altered by changing the layout of the corresponding seals of the respective wall, as explained in more detail below.

While described herein as providing a gas under pressure to the pockets 442, 446 prior to placing the medical device 900 within the cavity 422 of the pouch 400, it will be understood that the gas under pressure may be provided to the pockets 442, 446 after the medical device 900 has been received within the cavity 422, and during the final sealing process. In such a method, at least a portion of the first seal 424 between the first and second layers 410, 412 and the third seal 428 between the third and fourth layers 414, 416 will not completed until after the gas is provided to the pockets 442, 446, respectively.

A pouch 500 in accordance with another embodiment hereof is now shown in FIGS. 1 and 11-13. The pouch 500 includes a first edge 502, a second edge 504, a third edge 506, a fourth edge 508, a first layer 510, a third layer 514, a fourth layer 516, a first wall 518, a second wall 520, a cavity 522, a second seal 526, a third seal 528, a plurality of fifth seals 544, a first flange 530, and a second flange 532. These components of pouch 500 are similar to the similarly numbered items of the pouch 400. Therefore, a detailed explanation of the construction and alternatives of these similar components will not be described. However, in contrast to the pouch 400, the first wall 518 of the pouch 500 of FIGS. 11-13 includes only a first layer 510 and it is gas-permeable.

The first layer 510 is formed of a gas-permeable material such as, but not limited to a spun-bonded polyolefin marketed by DuPont under the name Tyvek® or medical grade paper. As the first wall 518 includes only the first layer 510, the first wall 518 does not include an inflated state or a pocket 540.

To assemble the pouch 500, the first layer wall 518 is superposed over the second wall 520 in the inflated state, which may be formed as described previously with respect to the second wall 420 of FIGS. 8-10. The superposed first and second walls 518, 520 are subjected to a sealing process to form the second seal 526 in the regions E, F, and G. Formation of the second seal 526 couples the first wall 518 to the second wall 520 and forms the cavity 522 between the first wall 518 and the second wall 520.

Figure 11:
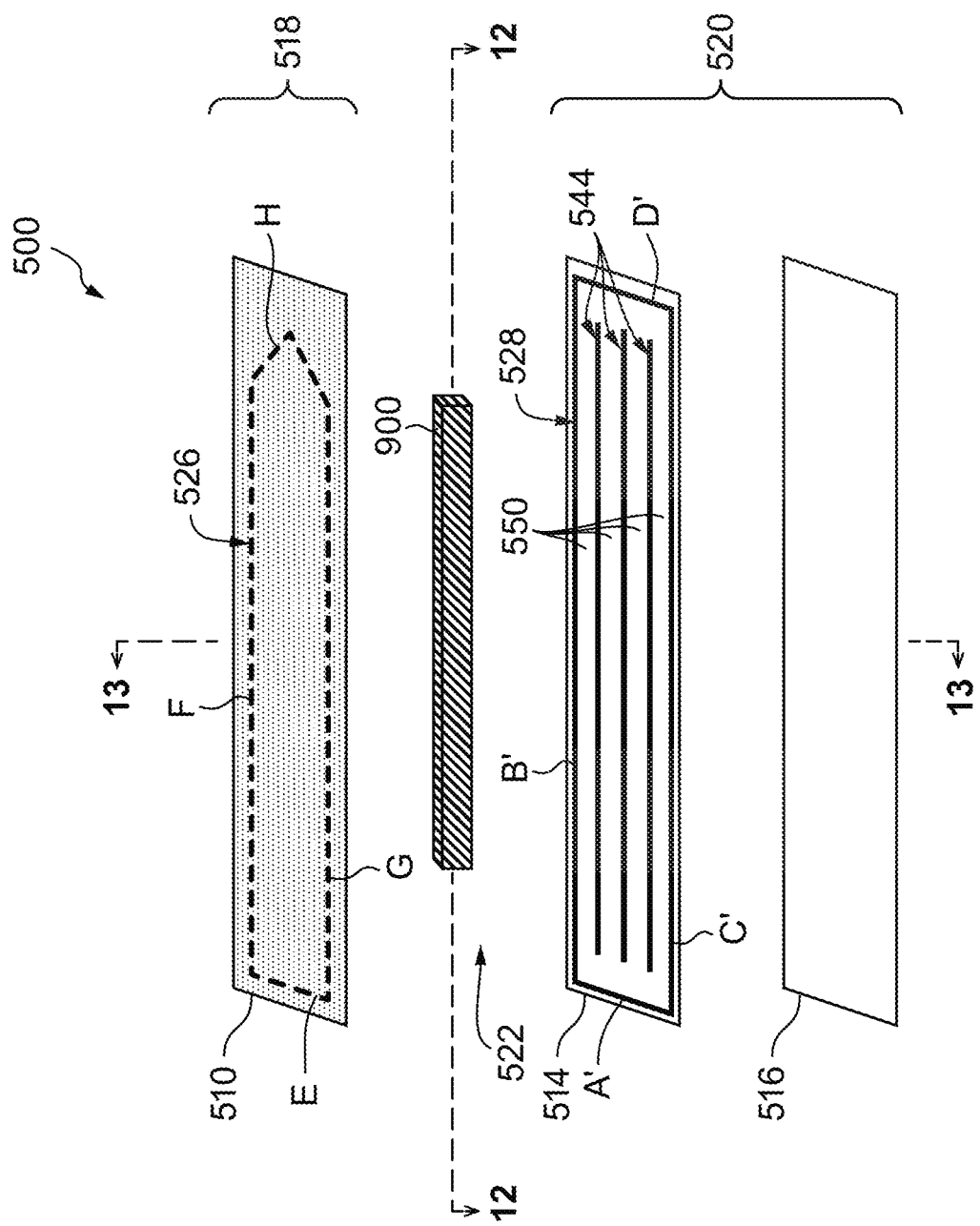
FIG. 11 depicts an exploded perspective view of a pouch in accordance with another embodiment hereof, wherein the pouch includes a pocket configured to receive a gas.
Figure 12:
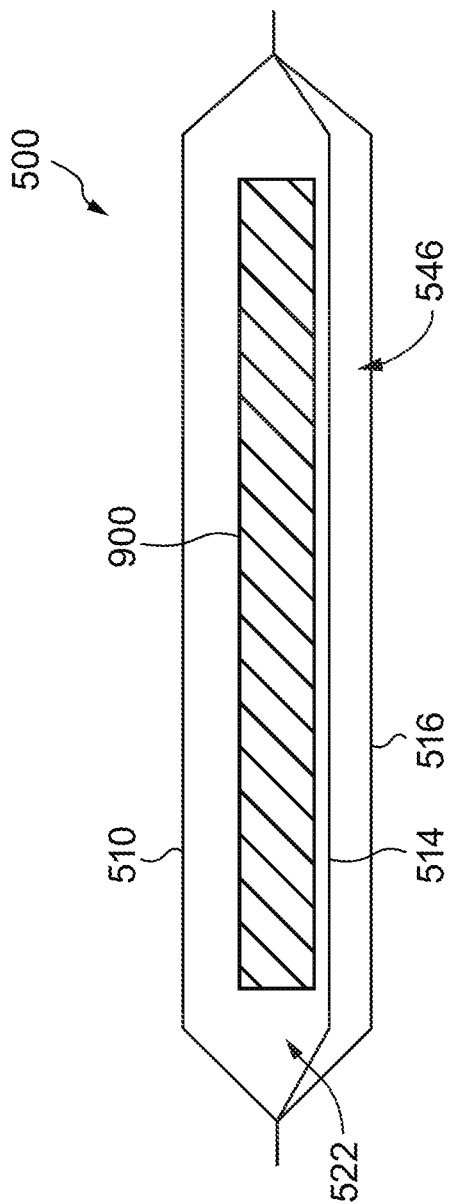
FIG. 12 depicts a longitudinal cross-sectional view of the pouch taken at line 12-12 of FIG. 11 with the pouch sealed.
Figure 13:
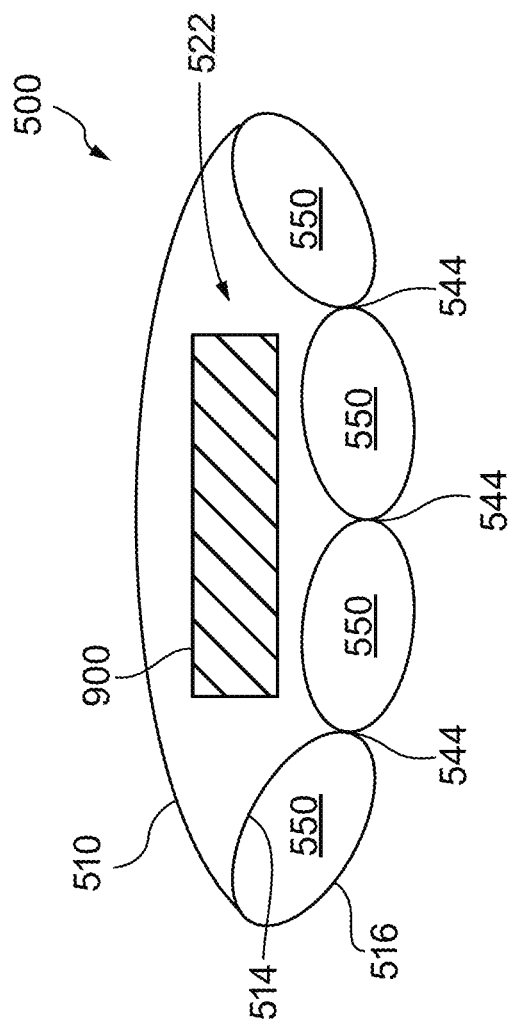
FIG. 13 depicts a cross-sectional view of the pouch taken at line 13-13 of FIG. 11 with the pouch sealed.

Similar to FIG. 8, FIG. 11 does not show the seal lines in all of the layers for clarity of the figure. Thus, the third seal 528 and the fifth seals 544 are shown only in the third layer 514, but they extend to both the third layer 514 and the fourth layer 516. Similarly, the second seal 526 is shown only in the second layer 512, but it extends to the first, third, and fourth layers 510, 514, and 516.

The multiple layers of the second wall 520 reduces the likelihood of a breach through both layers, in this embodiment the third layer 514 and the fourth layer 516, as described previously. Further the second wall 520 in the inflated state is configured to provide protection from physical damage to the medical device 900 during transportation, handling, storage and opening of the pouch 400.

A pouch 600 in accordance with another embodiment hereof is shown in FIGS. 1 and 14-16. The pouch 600 includes a first edge 602, a second edge 604, a third edge 606, a fourth edge 608, a first layer 610, a second layer 612, a third layer 614, a fourth layer 616, a first wall 618, a second wall 620, a cavity 622, a first seal 624, a second seal 626, a third seal 628, a plurality of fourth seals 640, a plurality of fifth seals 644, a pocket 642 of the first wall 618, a pocket 646 of the second wall 620, a first flange 630, and a second flange 632. These components of pouch 600 are similar to the similarly numbered items of the pouch 400. Therefore, a detailed explanation of the construction and alternatives of these similar components will not be described. However, the pouch 600 of FIGS. 14-16 further includes a perforation 652 through the first wall 618. The perforation 652 is sealed by a gas-permeable patch 654.

Figure 14:
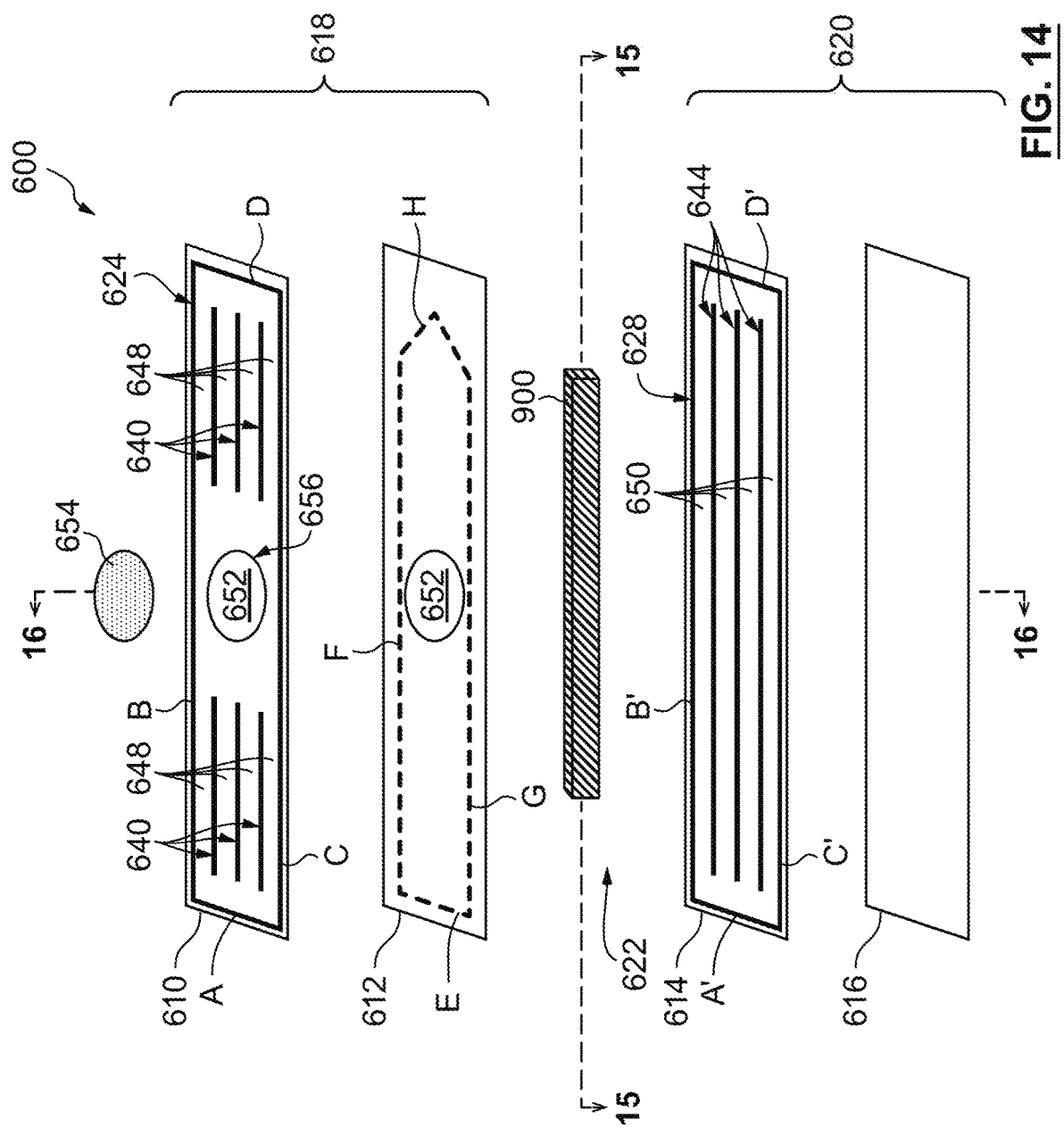
FIG. 14 depicts an exploded perspective view of a pouch in accordance with another embodiment hereof, wherein the pouch includes pockets and a perforation.

As best shown in FIG. 14, the first wall 618 includes the first layer 610 coupled to the second layer 612 by a first seal 624 in the marginal regions A, B, C, and D, a plurality of fourth seals 640, and a sixth seal 656. The pocket 642 is formed between the first and second layers 610, 612, and the first, fourth, and sixth seals 624, 640, 656. The sixth seal 656 defines the perforation 652 through the first wall 618. More specifically, the sixth seal 656 defines the perforation 652 through both the first layer 610 and the second layer 612. The first wall 618 is configured to receive a gas under pressure into the pocket 640.

The perforation 652 in the first wall 618 is configured to permit gases, such as gasses utilized for sterilization, to flow through the first wall 618 of the pouch 600 via the perforation 652, as described below. While shown with only one (1) perforation 652, it will be understood that more than one (1) perforation 652 may be utilized. Moreover, while the perforation 652 is shown in FIG. 14 with a generally circular shape, this is by way of example and not limitation, and the perforation 652 may have other shapes including oval, and rectangular shapes. Even further, the perforation 652 may be disposed at any location of the first wall 618 suitable for the purposes described herein (i.e., the perforation 652 must extend to the cavity 622), and is not restricted to the location shown in FIG. 14.

The patch 654 is a gas-permeable material such as materials described previously with respect to the first layer 110 of FIGS. 1-3. The patch 654 is disposed over the perforation 652 and is slightly larger in size then the perforation 652 such that the patch 654 may be coupled to the first wall 618 around the perimeter of the perforation 652. The patch 654 is configured to allow gases, such as those utilized in the sterilization process, to pass through the impermeable first and second layers 610, 612 of the first wall 618 via the perforation 652 to the cavity 622, but provide an effective barrier against the migration of micro-organisms, including bacteria. The patch 654 may be coupled to the first layer 610 by methods such as but not limited to adhesives, bonding, welding, fusing, heat sealing or any other suitable method.

Assembly of the pouch 600 is similar to the assembly of the pouch 400 described previously, therefore, only the differences in assembly will be described. The first layer 610 is superposed over the second layer 612 and subjected to a sealing process to couple the first layer 610 to the second layer 612. The first seal 624 is formed in the marginal regions A, B, C, and D, and the plurality of fourth seals 640 and the sixth heat seal 656 are formed between the first layer 610 and the second layer 612. A gas under pressure is provided to the pocket 642 of the first wall 618 to form and seal the wall 618 in the inflated state. The gas flows within the pocket 642 and around the plurality of fourth seals 440 and the sixth seal 656 to form a plurality of interconnected cushions, pillows or bubbles 448 and a relative recess in the first wall 618 at the perforation 652. The material of the first layer 610 and the second layer 612 at the perforation 652 within the sixth seal 656 may now be removed from the first wall 618 by methods such as, but not limited to die cutting, melting or other suitable methods. In other embodiments, the first and second layers 610, 612 may be provided with the perforations 652 provided and the sixth seal 656 may be made around such perforations 652.

The second wall 620 is assembled as described with respect to the second wall 420 of the pouch 400. Further, the first and second walls 618, 620 of the pouch 600 are then attached to each other as described previously with respect to the pouch 400 of FIGS. 8-10.

The multiple layers of the first wall 618 and the second wall 620 each reduce the likelihood of a breach in the corresponding wall, as described previously. Further, the first wall 618 in the inflated state and the second wall 620 in the inflated state each provide a cushion and additional protection to the medical device 900 stored within the pouch 600, as described previously with respect to the pouch 400 of FIGS. 8-10. The perforation 652 in the first wall 618 permits the use of gas processes for sterilization. The sterilizing gas may pass through the patch 654 to the cavity 622 and the medial device 900 disposed therein.

Similar to FIGS. 8 and 11, FIG. 14 does not show the seal lines in all of the layers for clarity of the figure. Thus, the first seal 624 and the fourth seals 640 are shown only in the first layer 610, but they extend to both the first layer 610 and the second layer 612 to couple them together. Similarly, the third seal 628 and the fifth seals 644 are shown only in the third layer 614, but they extend to both the third layer 614 and the fourth layer 616. Similarly, the second seal 626 is shown only in the second layer 612, but it extends to the first, second, third, and fourth layers 610, 612, 614, and 616.

Figure 17:
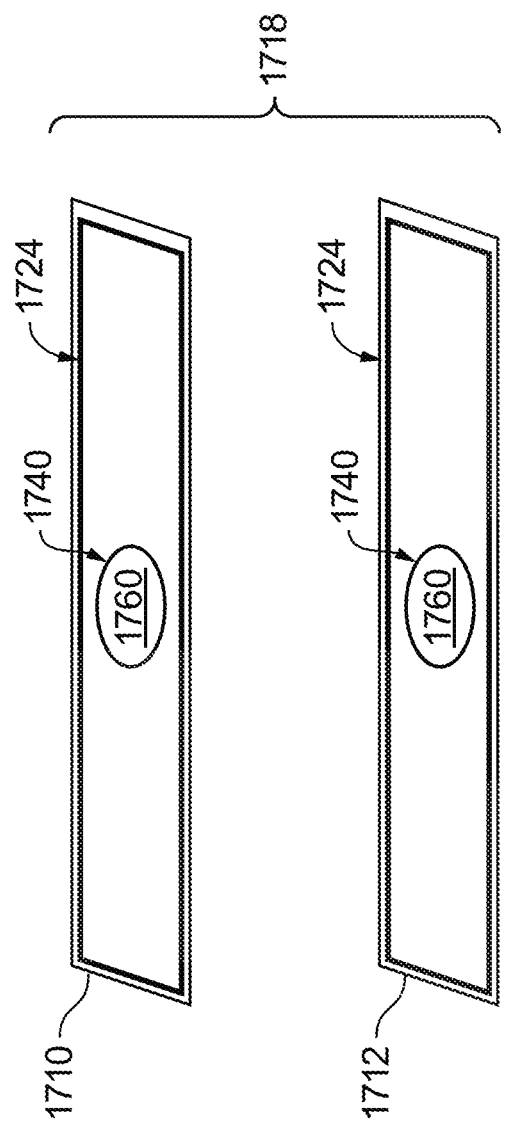
FIG. 17 depicts an exploded perspective view of a wall of a pouch according to an embodiment hereof, wherein the wall includes a pocket.

While the embodiments of the FIGS. 8-10, 11-13, and 14-16 have each shown wall with the fourth and/or fifth seals in a linear shape to form linearly aligned adjacent cushions, this is not meant to be limiting, and other shapes may be utilized. In an example shown in FIG. 17, a first wall 1718 includes a first layer 1710 and a second layer 1712. A first seal 1724 and a fourth seal 1740 attach the first layer 1710 to the second layer 1712. In the embodiment of FIG. 17, the fourth seal 1740 is circular in shape. When gas under pressure is supplied to a pocket 1742 of the first wall 1718, the gas fills the pocket 1742 between the first layer 1710, the second layer 1712, the first seal 1724, and the fourth seal 1740. The gas does not flow within the boundaries of the fourth seal 1740. Thus, a recess 1760 is formed within the first wall 1718 within the fourth seal 1740. The recess 1760 may be disposed at a desired location to provide additional clearance to a corresponding portion of a medical device (not shown in FIG. 17). Although described with one (1) recess 1760, this is by way of example and not exception and more than one (1) recess 1760 may be utilized. While a first wall 1718 has been utilized in the example described herein, this is by way of example and not limitation, and it will be understood that the example described herein is equally applicable to a second wall of a pouch of embodiments of the present disclosure.

Figure 18:
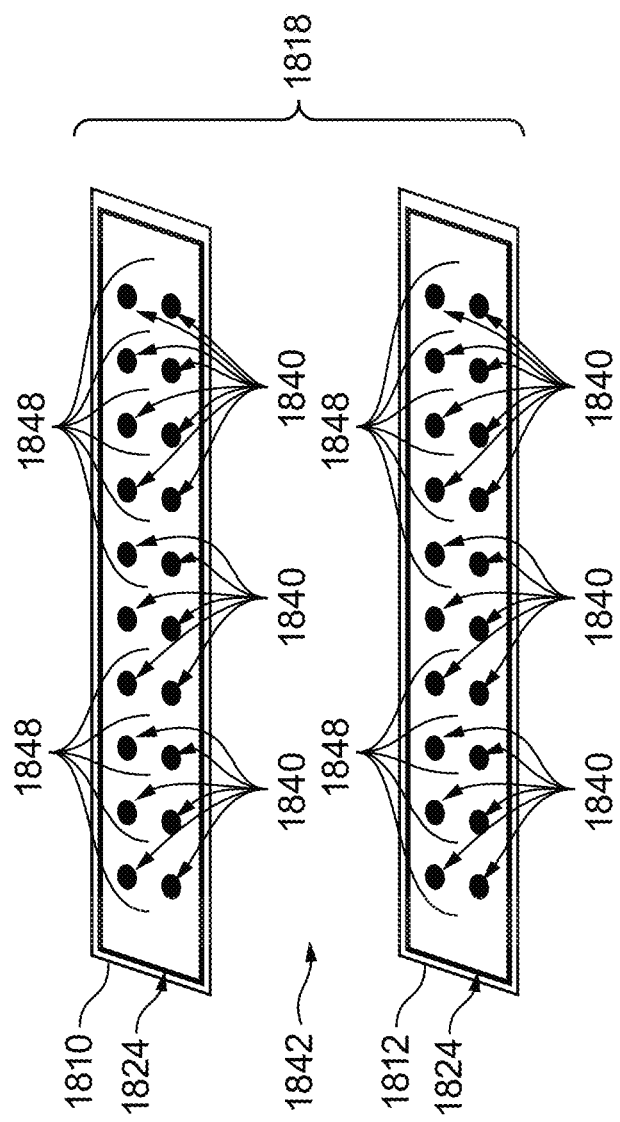
FIG. 18 depicts an exploded perspective view of a wall of a pouch according to another embodiment hereof, wherein the wall includes a pocket.

FIG. 18 shows another example of a first wall 1818 including a plurality of fourth seals 1840 in a mattress or quilted pattern. When gas under pressure is supplied to a pocket 1842 of the first wall 1818, the gas fills the pocket 1842 between the first layer 1810, the second layer 1812, the first seal 1824, and around the plurality of fourth seals 1840, creating a mattress pattern of cushions 1848. Although shown with a specific number of fourth seals 1840, this is by way of example and not limitation, and more or fewer fourth seals 1840 may be utilized to create more or fewer cushions 1848. Moreover, while described with a first wall 1818, it will be understood that the example described herein is equally applicable to a second wall of a pouch of embodiments of the present disclosure.

Although the formation of the various seals has been described specifically as separate processes, this is by way of example and not limitation, and it may be advantageous to form multiple seals simultaneously.

While the pouches described herein are shown with a generally rectilinear shape, this is by way of example and not limitation, and it will be understood that embodiments of pouches of the present disclosure may assume other shapes, such as oval, round, or virtually any desired shape.

Although described herein with specific examples of materials for the layers of the pouch embodiments, the specific materials of each layer of each embodiment may be selected based on the desired durability requirements of the pouch, permeability, and the sterilization method used.

While various embodiments according to the present invention have been described above, it should be understood that they have been presented by way of illustration and example only, and not limitation. Various changes in form and detail can be made therein without departing from the spirit and scope of the invention. Further, each feature of each of the embodiments described may be combined and/or interchanged with the features of any of the other embodiments described herein. Thus, the breadth and scope of the present invention should not be limited by any of the above-described exemplary embodiments, but should be defined only in accordance with the appended claims and their equivalents.

What is claimed is:

1. A flexible, sterilizable pouch comprising:
   a first wall including a first layer coupled to an adjacent second layer, the first and second layers being gas-impermeable;
   a second wall coupled to the first wall;
   a cavity defined between the first wall and the second wall, wherein the cavity is configured to receive a medical device; and
   at least one perforation extending through the first layer and the second layer configured to permit gases to flow through the first wall and into the cavity via the at least one perforation,
   wherein the pouch is configured to seal the medical device within the cavity,
   wherein the first wall further includes a pocket between the first layer and the second layer, wherein the pocket is configured to receive a gas under pressure,
   wherein when the gas is received within the pocket, the first wall transitions from an uninflated state to an inflated state, and
   wherein the first wall in the inflated state is configured to protect the medical device disposed within the cavity of the pouch.

2. The pouch of claim 1, wherein the pocket includes a plurality of cushions configured to protect the medical device disposed within the cavity of the pouch when the first wall is in the inflated state.

3. The pouch of claim 2, further comprising seals between the first layer and the second layer forming the plurality of cushions.

4. The pouch of claim 3, wherein the seals are disposed longitudinally.

5. The pouch of claim 3, wherein seals comprise point seals such that the plurality of cushions are in a mattress pattern.

6. The pouch of claim 1, wherein the first wall further includes a gas-permeable patch coupled to the first wall, wherein the patch is configured to seal the perforation.

7. The pouch of claim 1, wherein the second wall includes a third layer and a fourth layer such that each of the first and second walls includes two layers.

8. The pouch of claim 7, wherein the third layer is a gas-impermeable layer and the fourth layer is a gas-impermeable layer.

9. The pouch of claim 8, wherein the second wall further includes a pocket between the third layer and the fourth layer, wherein the pocket is configured to receive a gas under pressure,
   wherein when the gas is received within the pocket, the second wall transitions from an uninflated state to an inflated state; and
   wherein the second wall in the inflated state is configured to protect the medical device disposed within the cavity of the pouch.

10. The pouch of claim 9, wherein the pocket includes a plurality of cushions configured to protect the medical device disposed within the cavity of the pouch when the second wall is in the inflated state.

11. The pouch of claim 8, further comprising seals between the third layer and the fourth layer forming the plurality of cushions.

12. The pouch of claim 11, wherein the seals are disposed longitudinally.

13. The pouch of claim 11, wherein seals comprise point seals such that the plurality of cushions are in a mattress pattern.

14. The pouch of claim 1, wherein the first layer and the second layer are sealed together along the edges of the first layer and the second layer.

15. The pouch of claim 14, wherein the first layer and the second layer are configured to move relative to each other between the sealed edges.

16. The pouch of claim 1, wherein the first wall and the second wall are sealed to each other such that at least at one edge of the first and second walls, the seal is spaced from the at least one edge to form a first flange in the first wall and a second flange in the second wall for grasping to open the pouch.

17. The pouch of claim 1, wherein the second wall comprises a gas-permeable layer.

* * * * *